United States Patent [19]

Yoshikawa et al.

[11] Patent Number: 4,499,572
[45] Date of Patent: Feb. 12, 1985

[54] METHOD FOR READING INFORMATION OR DEFECT OUT OF ROTATING DISC

[75] Inventors: Shozi Yoshikawa, Hachioji; Masaharu Sakamoto, Tokyo; Hiroshi Kodama, Hachioji; Kunio Yamamiya, Tokyo; Kiichi Kato; Ken Ohsima, both of Hachioji, all of Japan

[73] Assignee: Olympus Optical Co., Ltd., Japan

[21] Appl. No.: 402,075

[22] Filed: Jul. 26, 1982

[30] Foreign Application Priority Data

Jul. 29, 1981 [JP] Japan .................................. 56-118647

[51] Int. Cl.$^3$ .............................................. G11B 7/00
[52] U.S. Cl. .................................... 369/111; 369/124
[58] Field of Search ............... 358/338, 339, 340, 342, 358/322, 907; 369/48, 49, 50, 59, 111, 58, 109, 100, 99, 124; 360/26, 27, 32, 73

[56] References Cited

U.S. PATENT DOCUMENTS

| | | | |
|---|---|---|---|
| 2,901,737 | 8/1959 | Stovall, Jr. ............................. | 360/73 |
| 4,142,210 | 2/1979 | Otobe et al. ......................... | 369/111 |
| 4,388,713 | 6/1983 | Tatsuguchi ......................... | 369/111 |
| 4,425,637 | 1/1984 | Tanaka et al. ..................... | 358/342 |

Primary Examiner—Donald McElheny, Jr.
Attorney, Agent, or Firm—Parkhurst & Oliff

[57] ABSTRACT

In order to read out information recorded on a disc rotating at a constant angular velocity by means of a pick-up head movably arranged in a disc radius direction, a head position on the disc is detected to obtain a position signal representing a distance from a disc center to the pick-up head, and then a pulse signal having a frequency corresponding to the position signal thus obtained is generated. A detection signal supplied from the pick-up head and the pulse signal are supplied to an AND gate and pulses of the gated out pulse signal are counted by a counter. The number of the counted pulses represents correctly a length of the information recorded on the disc irrespective of position of the information on the disc.

8 Claims, 17 Drawing Figures

FIG.1
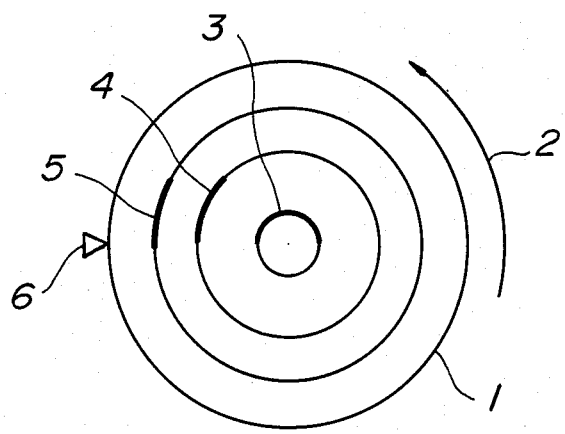
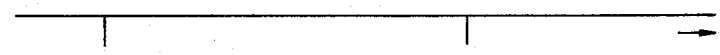
FIG.2A
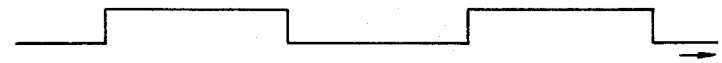
FIG.2B
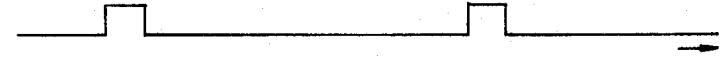
FIG.2C
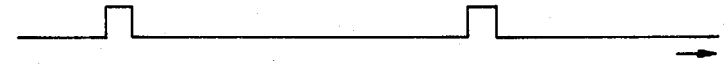
FIG.2D

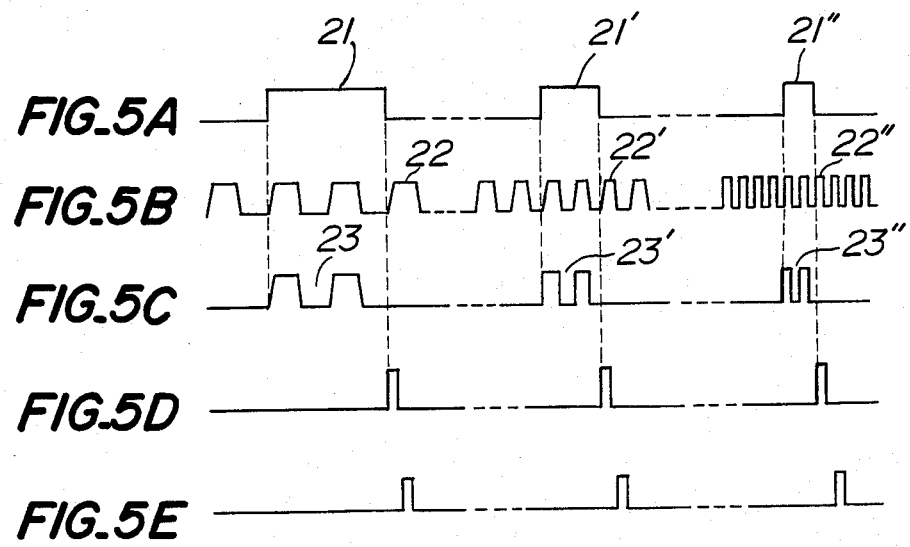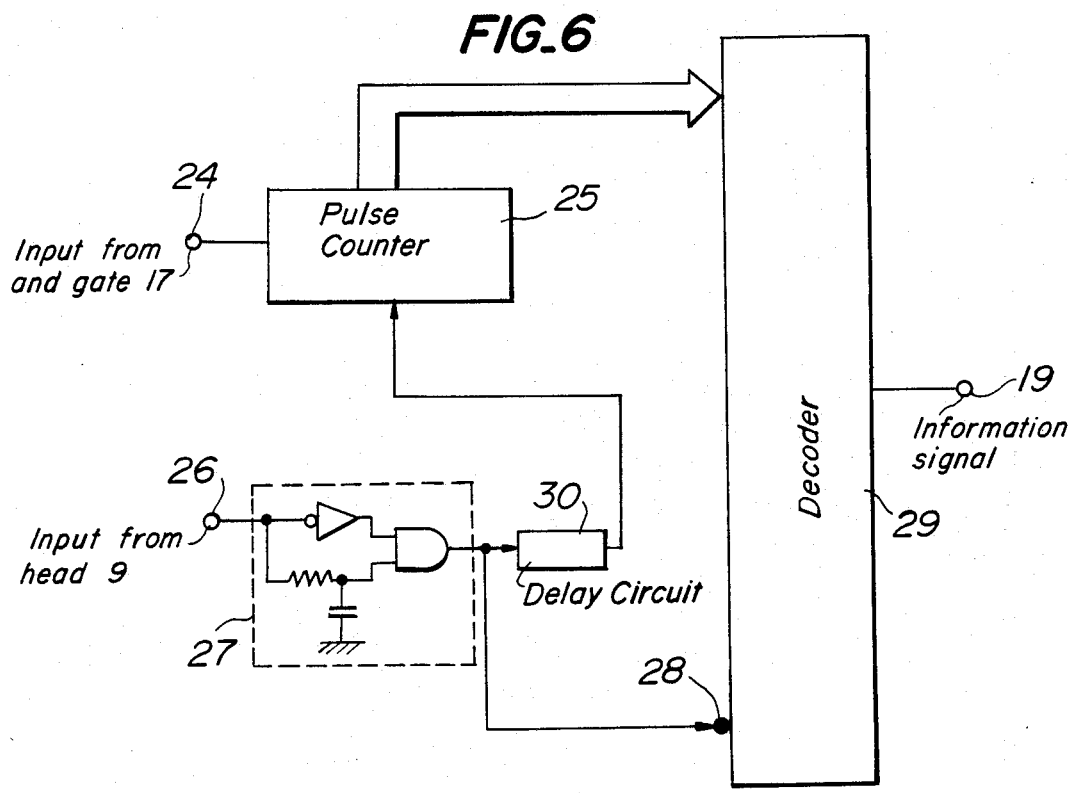

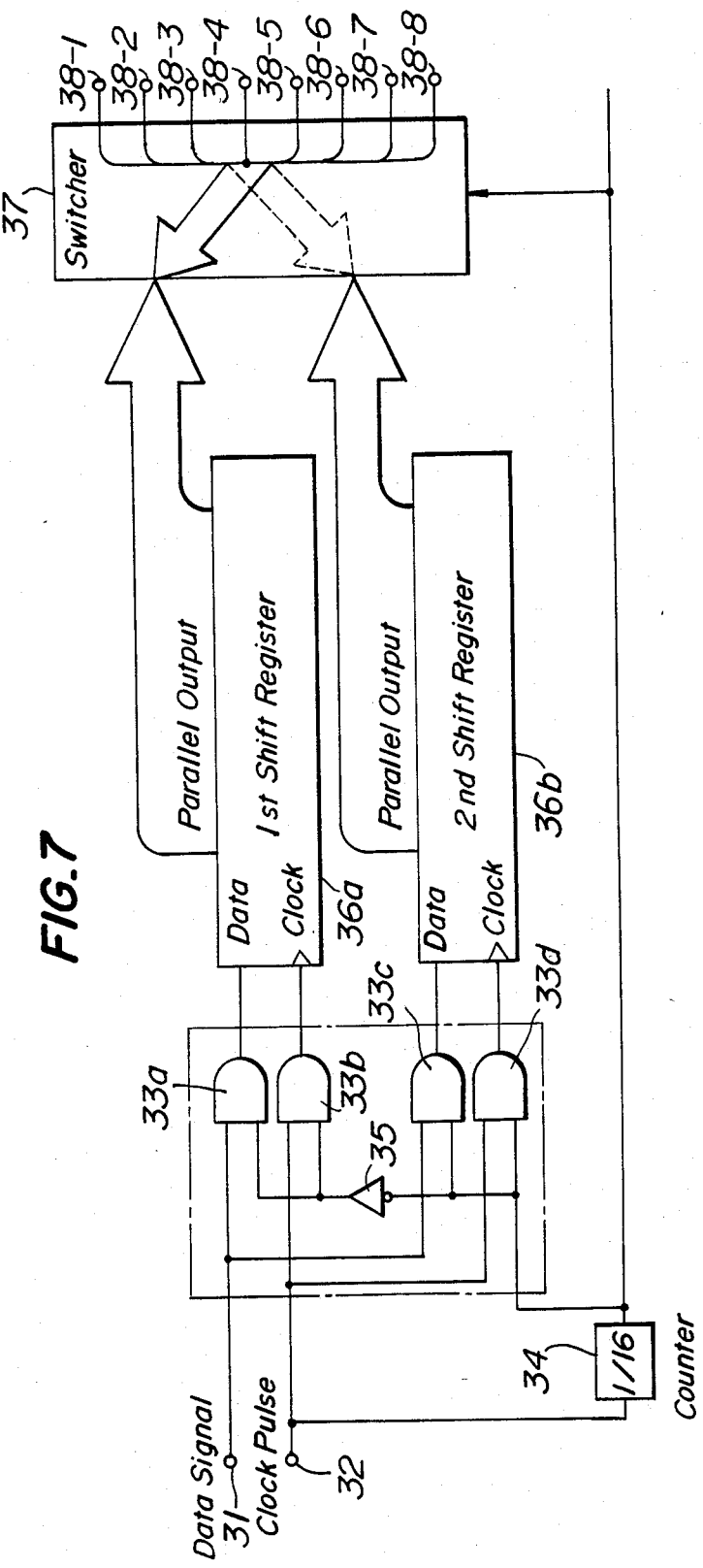

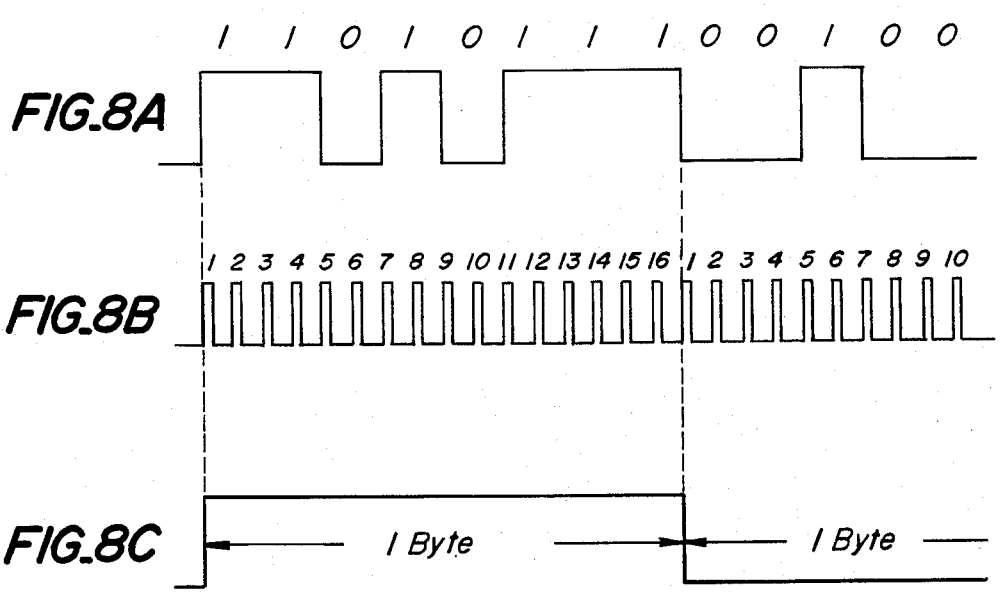

METHOD FOR READING INFORMATION OR DEFECT OUT OF ROTATING DISC

BACKGROUND OF THE INVENTION

The present invention relates to a method for reading information or detecting defects of a disc rotating at a constant angular velocity.

Recently there has been developed various kinds of systems in which information is recorded on a disc along spiral or concentric tracks and is read out of the rotating disc by means of a pick-up head which is moved in a radial direction of the disc. For instance, a video disc system has been developed in which a video signal is converted into a digital signal and the converted digital signal is recorded on an optical disc as a pit array along spiral or concentrical tracks and the recorded signal is then read out by means of a scanning light beam projected from a pick-up head which is moved in the radial direction of the disc. Upon reproduction, the video disc is rotated at a constant angular velocity. In order to obtain a reproduced digital signal having the same pulse duration as that of the original digital signal, pits on the disc must have different lengths at different positions viewed in its radial direction, because a linear velocity is different at the different positions on the disc. That is to say, the pits on inner tracks have a shorter length than on outer tracks. It should be noted that such a system does not utilize a recording density of the disc in an optimum manner. That is to say, on the outer tracks, the signal is not recorded with the highest recording density which can be obtained in the innermost track. In order to avoid such a drawback, it has been also known to record the signal on the disc in such a manner that the pits have the same length on both the outer and inner tracks. For example, such a system has been applied to a digital audio disc. In this system, in order to reproduce the signal correctly, the disc is rotated at a constant linear velocity, i.e. at different angular velocities. Contrary to this system, if the disc is rotated at a constant angular velocity, durations of reproduced pulses corresponding to the pits become different from each other at different points on the disc viewed in its radial direction.

Now this will be explained further in detail with reference to FIGS. 1 and 2A to 2D. In FIG. 1, a disc 1 is rotated in a direction shown by an arrow 2 at a constant angular velocity and information pits 3, 4 and 5 having the same length are recorded on different tracks. It should be noted that the pits are shown exaggeratedly. When these pits 3, 4 and 5 are picked up at a signal detecting position 6 on the basis of a rotation signal shown in FIG. 2A, there are obtained pit signals having durations which are inversely proportional to distances from a rotating center of the disc 1 to respective pits as shown in FIGS. 2B-2D. Therefore, if the information is defined by the pit lengths on the disc, the picked up information signals shown in FIGS. 2B-2D are detected to express different information in spite of the fact that the pits have been recorded as having the same information. For instance, a pulse width modulation signal could not be reproduced correctly.

In order to eliminate the drawback mentioned above, there has been developed a method for rotating the disc at a uniform linear velocity as mentioned above. In this method, a command signal for denoting a rotation speed of the disc to attain the uniform linear velocity must be recorded along respective tracks on the disc, and upon the reproduction the command signal is at first read out by the pick-up head, and then a rotating speed of the disc is controlled according to the picked-up command signal so as to obtain a required linear velocity at respective positions on the disc. However, if the pick-up head is moved abruptly in the radial direction, information reading can not be initiated until the disc is rotated at the required linear velocity by means of a disc rotating mechanism having a large time lag or inertia. Therefore, an access time might be prolonged to a great extent. Moreover, if the command signal is not recorded on the disc, the control of the disc rotation could not be effected at all. For instance, in case of detecting defects on a disc in which information has not yet been recorded, the disc could not be rotated at a constant linear velocity. Further, when defects on silicon wafers for use in manufacturing semiconductor devices are to be detected by concentrically or spirally scanning the wafer surfaces, the wafers could not be rotated at a constant linear velocity, because the command signal could never be recorded thereon. In such a defect detection, it is important to detect size or dimension of defects precisely, but in the known methods utilizing the constant angular velocity, the size or dimension of defects could not be detected accurately.

SUMMARY OF THE INVENTION

The present invention has for its object to eliminate the drawbacks mentioned above and to provide a method for reading out information recorded on a disc which is rotated at a constant angular velocity to obtain a reproduced signal which correctly represents lengths of information on the disc.

It is another object of the invention to provide a method for detecting defects on a disc such as original discs for use in manufacturing video and audio discs and silicion wafers for use in manufacturing semiconductor devices, to obtain a defect signal which represents the size or dimension of defects, while the disc is rotated at a constant angular velocity.

It is still another object of the invention to provide a method for precisely reading information or defects out of a disc rotating at a constant angular velocity.

It is still another object of the invention to provide a method for reading information or defects out of a disc rotating at a constant angular velocity to obtain numerical data which represents lengths of information or defects.

According to the invention, a method of detecting information or defects out of a disc by rotating the disc at a constant angular velocity with respect to a pick-up head which is moved in a radial direction of the disc and scans the disc along spiral or concentric tracks to produce a detection signal, comprises the steps of detecting a position of the pick-up head above the disc to produce a position signal;

generating in response to said position signal a pulse signal having a frequency which is proportional to the distance from a center of the disc to the pick-up head; and deriving an output signal from the detection signal supplied from the pick-up head under the control of said pulse signal.

BRIEF DESCRIPTION OF THE DRAWINGS

FIG. 1 is a plan view schematically showing information pits which are recorded at different tracks on a disc and have the same data length;

FIGS. 2A to 2D are waveforms of information signals read out of the disc in FIG. 1, while the disc is rotated at a constant angular velocity;

FIGS. 5A to 5E are waveforms for explaining an operation of the apparatus of FIG. 3;

FIG. 6 is a block diagram depicting one embodiment of a signal processing circuit shown in FIG. 3;

FIG. 7 is a block diagram showing another embodiment of the signal processing circuit according to the invention; and FIGS. 8A to 8C are waveforms for explaining the operation of the circuit shown in FIG. 7.

DESCRIPTION OF THE PREFERRED EMBODIMENTS

Figure 3:
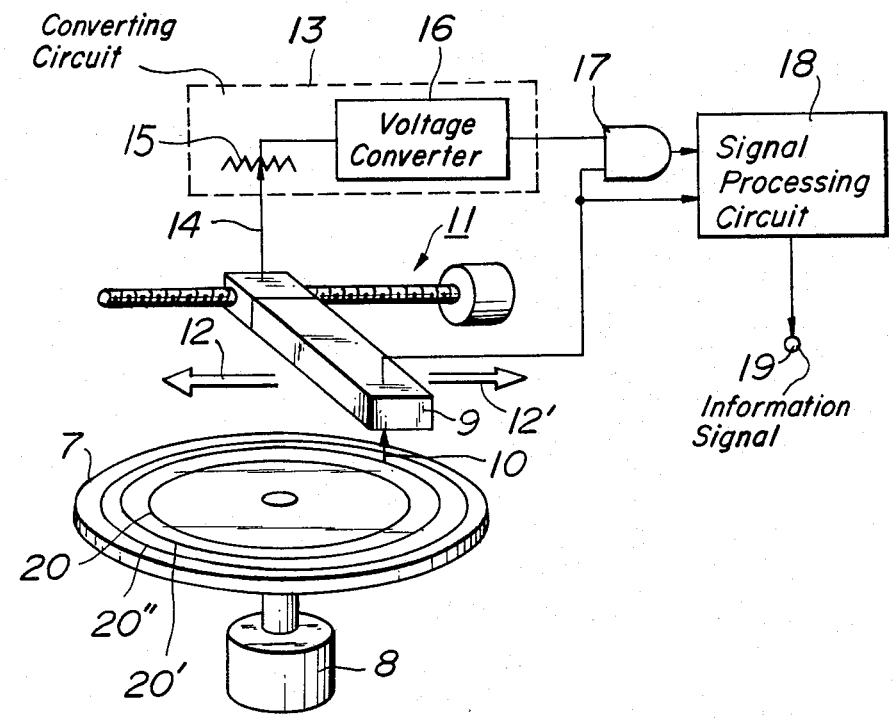
FIG. 3 is a schematic view depicting one embodiment of an apparatus for performing the method according to the invention.

FIG. 3 is a schematic view showing one embodiment of an apparatus for performing the method according to the invention. In FIG. 3, a disc-shaped record medium (hereinafter called "disc") 7 is rotated at a constant angular velocity by a rotation driving mechanism 8 such as a motor, and an information pick-up head 9 comprising, for example, a light source, an optical system, and a light receiving element serves to project a light flux emitted from the light source onto the disc as a light spot, to receive a light flux 10 reflected by the disc 7 by means of the light receiving element, and finally to convert the received light flux photoelectrically into an output signal. The pick-up head 9 is moved in a disc radial direction as shown by arrows 12, 12' by means of a head moving mechanism 11 comprising a motor for rotating a lead screw. The apparatus further comprises a converting circuit 13 for converting the head position with respect to the disc 7 into a pulse signal. For this purpose, the converting circuit comprises a head position detector 14, a head position converter 15, and a voltage converter 16 which generates a pulse signal having a frequency in proportion to a distance from the rotation center or a periphery of the disc 7 to the head position measured in the radial direction of the disc. In the head position converter 15, a control voltage is produced in proportion to the aforementioned distance derived from the head position detector 14 coupled with the pick-up head 9, and then the control voltage is converted into the pulse signal by the voltage converter 16.

Figure 4:
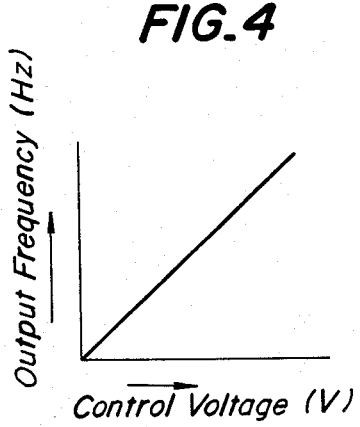
FIG. 4 is a graph showing voltage-frequency characteristics of a converting circuit in FIG. 3.

As for the head position converter 15, for example, use may be made of a potentiometer in which a volume thereof is varied corresponding to a head positioning signal derived from the head position detector 14, and thus the control voltage corresponding to the pick-up head position is obtained from the potentiometer. Moreover, it is necessary that the voltage converter 16 has a linear voltage-frequency characteristic as shown in FIG. 4. The voltage converter 16 may be made of a sweep oscillator of voltage controlled type (herein referred to as the sweep oscillator). Then the oscillation frequency of the sweep oscillator 16 is varied in direct proportion to the position of the pick-up head 9 on the disc 7 between the minimum and maximum frequencies.

The information signal derived from the pick-up head 9 and the pulse signal produced from the converting circuit 13 are supplied to an AND gate 17 and pulses gated out by the information signal from the head 9 are supplied to a signal processing circuit 18. Then the signal processing circuit 18 produces a desired information signal at an output terminal 19.

Now the operation of the apparatus will be explained. As mentioned above, the disc 7 is rotated at the constant angular velocity. It is assumed that information pits recorded on different tracks 20, 20', 20" of the disc 7 have the same data length. When these pits are read out by the pick-up head 9, there are obtained pit pulses as shown in FIG. 5A by 21, 21' and 21". Since the length of the pits is very small as compared with the radius of the disc, it is recognized that a time duration of the detected pit pulses is inversely proportional to distances from the tracks 20, 20' and 20" to the center of disc. The output voltage of the head position converter 15 is gradually increased in proportion to the distance from the rotating center to the position of the pick-up head 9 above the disc 7 and thus the output frequency of the sweep oscillator 16 is increased corresponding to the time duration of the detected pit signals as shown in FIG. 5B by 22, 22' and 22". Therefore, the number of pulses produced in the durations of the detected output signals 21, 21' and 21' is always kept the same number. Accordingly, when the pulse signal supplied from the sweep oscillator 16 and the detected pit signal from the pick-up head 9 are supplied to the AND gate 17 to calculate the logical product thereof, it is possible to derive equivalent signals 23, 23' and 23" each having the same number of pulses as shown in FIG. 5C. In this manner, the original information can be correctly derived from the information signals 21, 21' and 21" each having the same data length and recorded on the different tracks on the disc 7, while the disc is roated at the constant angular velocity.

FIG. 6 is a block diagram showing one embodiment of the signal processing circuit 18 according to the invention. The pulses gated out by the AND gate 17 are supplied to a pulse counter 25 through a pulse signal input terminal 24. The detected pit signals shown in FIG. 5A from the pick-up head 9 are supplied to a differential circuit 27 through a pulse signal input terminal 26 so as to generate pulses at trailing edges thereof as shown in FIG. 5D. Then, the pulses thus obtained are supplied through a timing pulse output terminal 28 to a decoder 29 to which a parallel data output from the pulse counter 25 is also supplied. In this manner the parallel data output of the counter 25 is written in the decoder 29 in synchronism with the pulse and thus, the information signals having the original data lengths are correctly reproduced in the decoder 29. Moreover, in order to reset the pulse counter 25 just after the count value has been written in the decoder 29, the output pulse from the differential circuit 27 is supplied to a delay circuit 30 to produce a slightly delayed pulse shown in FIG. 5E and the pulse counter 25 is reset by the delayed pulse.

FIG. 7 is a block diagram illustrating another embodiment of the signal processing circuit for deriving an original bit signal from a read out signal, and FIGS. 8A to 8C are waveforms for explaining an operation thereof. The circuit comprises a data input terminal 31 for receiving a read out data signal shown in FIG. 8A and a clock pulse input 32 for receiving a clock pulse shown in FIG. 8B generated from the sweep oscillator 16 in the converting circuit 13. The data signal is parallelly supplied to AND gates 33a and 33c, and the clock pulse is also parallelly supplied to AND gates 33b and 33d. As shown in FIGS. 8A to 8C, one byte data is composed of eight bits and one bit length corresponds to two clock pulses. Therefore, sixteen clock pulses are produced in each byte data. The clock pulse is further supplied to a clock counter 34 for dividing the clock pulses by sixteen and then the counter 34 produces an output signal shown in FIG. 8C. This output signal is supplied to the AND gates 33c and 33d directly, and to the AND gates 33a and 33b via an inverter 35. Therefore, when the output signal from the counter 34 is in a logical low level, the AND gates 33a and 33b are made enable and the data signal passing through the AND gate 33a is supplied to a first shift register 36a under the control of clock pulses supplied via the AND gate 33b. The shift register 36a has a capacity for storing sixteen bits therein. The next data of one byte is stored in a second shift register 36b having an identical construction with the first register 36b. During the time period, the bit data stored in the first shift register 36a is read out parallelly via a switcher 37 which is driven by the output phase signal from the counter 34. Since the data of one byte is composed of eight bits, odd or even eight bits of the shift register are read out via the switcher 37. In this manner, the original data signal can be correctly reproduced at output terminals 38-1 to 38-8 in a continuous manner.

As clearly seen from the embodiment mentioned above, according to the invention, it is possible to read out correctly the information recorded on the disc rotating at the constant angular velocity. This method may be advantageously applied to the disc in which a pulse width modulation signal has been recorded. Furthermore, the method according to the invention may preferably be applied to detect defects for a disc-shaped member such as original discs for use in manufacturing video discs and silicon wafers for use in manufacturing semiconductor devices, and it is possible to obtain a defect signal which represents the size or dimension of the defects precisely.

Moreover, in the method according to the invention, sincde it is not necessary to vary the angular velocity during the reproduction, even if the pick-up head is moved abruptly, the information reading can be initiated soon and thus, a very short access time can be attained. Further, in the method according to the invention, since the pit length on outer tracks need not be prolonged, the information can be recorded with the optimum density.

It should be noted that the present invention is not limited to the embodiment explained above, but may be modified in various ways. For instance, it is a matter of course that the disc may be scanned concentrically instead of spirally. Moreover, in the above explained embodiment, use is made of the optical disc, but any other type of record discs such as a magnetic disc, and an electrostatic capacitance type disc may be used.

What is claimed is:

1. A method of detecting information or defects out of a disc by rotating the disc at a constant angular velocity with respect to a pick-up head which is moved in a radial direction of the disc and scans the disc along spiral or concentric tracks to produce a detection signal, comprising the steps of detecting a position of the pick-up head above the disc to produce a position signal;

generating in response to said position signal a pulse signal having a frequency which is proportional to a distance from a center of the disc to the pick-up head; and deriving an output signal from the detection signal supplied from the pick-up head under the control of said pulse signal.

2. A method according to claim 1, wherein said output signal deriving step comprises a step of gating the pulse signal by means of the detection signal, and a step of counting by a counter the number of gated out pulses to derive the output signal having a numeral value representing a length of detected information or defect.

3. A method according to claim 1, wherein said output signal deriving step comprises a step of storing serially the detection signal in a shift register, while the pulse signal is used as a shift clock pulse.

4. A method according to claim 3, wherein said detection signal stored in the shift register is read out parallelly.

5. A method according to claim 1, wherein said step of detecting the position of the pick-up head comprises a step of generating a voltage having an amplitude which corresponds to the pick-up head position, and said pulse signal generating step comprises a step of generating said pulse signal from a voltage controlled oscillator which is controlled by said voltage.

6. A method according to claim 5, wherein the amplitude of said voltage is directly proportional to the distance between the pick-up head and the disc center and said frequency of the pulse signal is also directly proportional to said voltage.

7. A method according to claim 6, wherein said voltage is derived from a potentiometer whose variable arm is coupled with said pick-up head.

8. A method according to claim 2, wherein said counter is preset by an edge signal which is derived from the detection signal and is delayed by a short time.

* * * * *